US010087395B2

(12) United States Patent
Pelzer et al.

(10) Patent No.: US 10,087,395 B2
(45) Date of Patent: Oct. 2, 2018

(54) USE OF HEXADECA-8,15-DIENAL AS AROMA CHEMICAL

(71) Applicant: BASF SE, Ludwigshafen (DE)

(72) Inventors: Ralf Pelzer, Fürstenberg (DE); Frauke Thrun, Mannheim (DE); Joaquim Henrique Teles, Waldsee (DE); Albert Werner, Frankenthal (DE); Stephan Maurer, Neustadt (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/518,791

(22) PCT Filed: Oct. 13, 2015

(86) PCT No.: PCT/EP2015/073662
§ 371 (c)(1),
(2) Date: Apr. 13, 2017

(87) PCT Pub. No.: WO2016/059042
PCT Pub. Date: Apr. 21, 2016

(65) Prior Publication Data
US 2017/0362532 A1    Dec. 21, 2017

(30) Foreign Application Priority Data

Oct. 14, 2014  (EP) .................... 14188771

(51) Int. Cl.
| | | |
|---|---|---|
| *C11B 9/00* | (2006.01) |
| *C07C 45/82* | (2006.01) |
| *A61L 9/01* | (2006.01) |
| *A23L 29/00* | (2016.01) |
| *A61K 47/08* | (2006.01) |
| *A61K 8/33* | (2006.01) |
| *C11D 3/50* | (2006.01) |
| *A61Q 13/00* | (2006.01) |

(52) U.S. Cl.
CPC ............ *C11B 9/0015* (2013.01); *A23L 29/00* (2016.08); *A61K 8/33* (2013.01); *A61K 47/08* (2013.01); *A61L 9/01* (2013.01); *A61Q 13/00* (2013.01); *C07C 45/82* (2013.01); *C11D 3/50* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,925,367 A | 7/1999 | Angst et al. |
| 8,957,244 B2 | 2/2015 | Schneider et al. |
| 8,987,497 B2 | 3/2015 | Vautravers et al. |
| 9,139,548 B2 | 9/2015 | Yang et al. |
| 9,217,121 B2 | 12/2015 | Rudenauer et al. |
| 9,340,754 B2 | 5/2016 | Rudenauer et al. |
| 9,347,596 B2 | 5/2016 | Wortmann et al. |
| 9,371,239 B2 | 6/2016 | Parvulescu et al. |
| 9,428,438 B2 | 8/2016 | Fries et al. |
| 9,464,029 B2 | 10/2016 | Boehling et al. |
| 9,640,839 B2 | 5/2017 | Porta Garcia et al. |
| 2010/0191018 A1 | 7/2010 | Teles et al. |
| 2014/0047837 A1 | 2/2014 | Wortmann et al. |
| 2014/0182720 A1 | 7/2014 | Wortmann et al. |
| 2014/0202153 A1 | 7/2014 | Wortmann et al. |
| 2015/0368115 A1 | 12/2015 | Parvulescu et al. |
| 2016/0172708 A1 | 6/2016 | Porta Garcia et al. |
| 2016/0176834 A1 | 6/2016 | Teles et al. |
| 2016/0176835 A1 | 6/2016 | Riedel et al. |
| 2016/0185741 A1 | 6/2016 | Teles et al. |
| 2016/0185762 A1 | 6/2016 | Teles et al. |
| 2016/0213582 A1 | 7/2016 | Rudenauer et al. |
| 2016/0250624 A1 | 9/2016 | Parvulescu et al. |
| 2016/0256859 A1 | 9/2016 | Parvulescu et al. |
| 2016/0264543 A1 | 9/2016 | Vautravers et al. |
| 2016/0279621 A1 | 9/2016 | Parvulescu et al. |
| 2016/0312149 A1 | 10/2016 | Vautravers et al. |
| 2016/0318860 A1 | 11/2016 | Vautravers et al. |
| 2016/0332152 A1 | 11/2016 | Parvulescu et al. |
| 2016/0332944 A1 | 11/2016 | Rudenauer et al. |
| 2016/0362387 A1 | 12/2016 | Teles et al. |
| 2016/0368843 A1 | 12/2016 | Teles et al. |
| 2016/0368887 A1 | 12/2016 | Dehn et al. |
| 2017/0009749 A1 | 1/2017 | Wortmann et al. |
| 2017/0010024 A1 | 1/2017 | Wortmann et al. |
| 2017/0037021 A1 | 2/2017 | Stork et al. |
| 2017/0107168 A1 | 4/2017 | Vautravers et al. |

FOREIGN PATENT DOCUMENTS

EP    0376888 A1    7/1990

OTHER PUBLICATIONS

International Preliminary Examination Report for PCT/EP2015/073662 and Applicant response (in German) dated Sep. 16, 2016.
International Search Report for PCT/EP2015/073662 dated Jan. 25, 2016.
U.S. Appl. No. 15/308,755, filed Nov. 3, 2016, Vautravers et al.
U.S. Appl. No. 15/514,101, filed Mar. 24, 2017, Stork et al.

*Primary Examiner* — Bong-Sook Baek

(74) *Attorney, Agent, or Firm* — Drinker Biddle & Reath LLP

(57) ABSTRACT

The present invention relates to the use of hexadeca-8,15-dienal or of a substance mixture which comprises this compound as aroma chemical, in particular as fragrance, or formulation auxiliary; and also to processes for its preparation, moreover aroma substance compositions and compositions comprising hexadeca-8,15-dienal.

8 Claims, No Drawings

USE OF HEXADECA-8,15-DIENAL AS AROMA CHEMICAL

CROSS-REFERENCE TO RELATED APPLICATIONS

This application is a national stage application (under 35 U.S.C. § 371) of PCT/EP2015/073662, filed Oct. 13, 2015, which claims benefit of European Application No. 14188771.1, filed Oct. 14, 2014, both of which are incorporated herein by reference in their entirety.

The present invention relates to the use of a mixture of (E/Z)-hexadeca-8,15-dienal or of a substance mixture which comprises this compound as aroma chemical, in particular as fragrance, or formulation auxiliary; and also to processes for its preparation, moreover aroma substance compositions and compositions which comprise hexadeca-8,15-dienal.

BACKGROUND OF THE INVENTION

Despite a large number of existing fragrances, there is a constant need in the perfume industry for new fragrances which, over and above their primary, namely odiferous (olfactory) properties, have additional positive secondary properties, such as e.g. an efficient mode of preparation, a higher stability under certain application conditions, a higher range or a better staying power, or else lead to better sensory profiles as a result of synergy effects with other fragrances.

In the perfume industry, there is also fundamentally a need for other fragrances which are suitable for producing fragrance compositions and/or perfumed articles. In particular, there is a need for fragrances which, by virtue of the technical properties mentioned above, lead to an increased benefit in fragrance compositions. Thus, for example as a result of using fragrances with an efficient mode of preparation, a higher stability and a better sensory profile, it is possible to optimize and/or minimize the amounts used and the number of fragrances in corresponding formulations, which leads to a sustainable conservation of resources during the perfuming of consumer articles.

The main ingredient of naturally occurring musk is muscone. Synthetically produced muscone is a racemate, i.e. a 1:1 mixture of the cyclic ketones (R)-(−)-3-methylcyclopentadecanone and (S)-(+)-3-methylcyclopentadecanone.

In the field of fragrances and scents, there is already a large number of musk-like components, e.g. habanolide, Exaltolid®, muscenone and Globanon®. These compounds belong to the class of saturated/unsaturated carbonyl-containing macrocycles. Besides the cyclic musk-like fragrances, there are no or only a few long-chain (Helvetolid®, Cyclomusk®) saturated and/or unsaturated carbonyl compounds which have this olfactory property.

In particular, there is a need for further fragrances and fragrance compositions with a musk note.

U.S. 2010/0191018 describes the oxidation of various polyunsaturated cyclic aliphatics, such as e.g. cyclohexadeca-1,9-diene, with dinitrogen monoxide. As by-product, the formation of hexadeca-8,15-dienal is observed here. Its suitability as fragrance with a musk character, however, has still not been described.

SUMMARY OF THE INVENTION

Surprisingly, the above object was achieved through the provision of hexadeca-8,15-dienal. The isolation of a mixture of (E/Z)-hexadeca-8,15-dienal was surprisingly possible from the reaction mixture of the oxidation of cyclohexadecadiene with dinitrogen monoxide. The mixture is characterized by a marked musk scent.

DETAILED DESCRIPTION OF THE INVENTION a) General Definitions

In the context of the invention, "hexadeca-8,15-dienal" comprises both one of the two stereoisomeric forms (i.e. the 8-(E) and also the 8-(Z) form) individually or as a mixture of these two stereoisomers ((E/Z)-hexadeca-8,15-dienal), but also substance mixtures which comprise "essentially", i.e. with a weight fraction of more than 90%, in particular more than 95% and in particular more than 96, 97, 98 or 99%, "hexadeca-8,15-dienal" in stereoisomerically pure form or as stereoisomer mixture. Unless stated otherwise, "hexadeca-8,15-dienal" in the context of the invention thus means a stereoisomer mixture of the 8-(E) and also the 8-(Z) form, preferably in a molar ratio of E to Z of about 1:5 to 5:1, such as e.g. about 1:2 to 2:1 or in particular about 1:1.7613035220065

The 8-(E) form has the following structure:

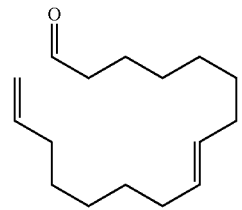 [SMILES: C=CCCCCC/C=C/CCCCCCC=O]

An "aroma chemical" is a generic term for compounds which can be used as "fragrance" and/or as "flavoring".

In the context of the present invention, "fragrance" is to be understood as meaning natural or synthetic substances with an intrinsic odor.

In the context of the present invention, "flavoring" is to be understood as meaning natural or synthetic substances with an intrinsic taste.

In the context of the present invention, the "odor" or the "olfactory perception" is the interpretation of the sensory stimuli which are sent from the chemoreceptors in the nose or other olfactory organs to the brain of a living being. The odor can consequently be a sensory perception by the nose of fragrances which takes place upon breathing in. In this case, the air serves as the odor carrier.

In the context of the present invention, "scent" is to be understood as meaning a pleasant smelling odor. The same applies to a "scent substance" according to the invention.

In the context of the present invention, a "perfume" is a mixture of fragrances and carriers, such as in particular an alcohol.

In the context of the present invention, a "perfume composition" is a perfume which comprises different amounts of individual components matched to one another to be in harmony. The properties of the individual constituents are utilized in order to provide a new overall image in the combination, where the characteristics of the ingredients retire into the background, but without being suppressed.

In the context of the present invention, a "perfume oil" is a concentrated mixture of several fragrances which are used e.g. in alcoholic solutions for the perfuming of various products.

In the context of the present invention, a "scent theme" is the predominant scent note in a fragrance composition.

For the purposes of the present invention, a "musk note" or "musk scent" is to be understood as meaning an odor which is similar to the odor of natural musk or to that of its constituents.

In the context of the present invention, the "top note" is the first phase of the scent progression of a perfume. It plays a decisive role in the first impression, upon opening the bottle and when applying the perfume to the skin. The aim of the top note is to arouse interest in the perfume generally and to ensure attention. Consequently, an extraordinary character is often more important than a polished harmony. The top note is naturally determined by readily volatile fragrances.

In the context of the present invention, "modifying" means to provide the basic theme of a fragrance composition with additional or different accords and odor nuances.

In the context of the present invention, "accords" are produced by combining different fragrances which thus combine to give new odor images. The number of fragrances used can range from two to several hundred.

In the context of the present invention, an "organoleptically/sensorally effective amount" is the amount of a fragrance which suffices to have a stimulatory effect on a sensory organ or stimulatory effect on a sensory receptor.

b) Specific Embodiments of the Invention

The present invention relates in particular to the embodiments below:
1. The use of hexadeca-8,15-dienal of the formula I

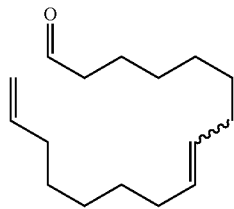

(I)

((E/Z)-hexadeca-8,15-dienal or (E)-hexadeca-8,15-dienal or (Z)-hexadeca-8,15-dienal) or of a substance mixture which comprises this compound as aroma chemical, in particular as fragrance, or as formulation auxiliary.
2. The use according to embodiment 1 in compositions selected from perfumes, detergents and cleaners, cosmetic compositions, bodycare compositions, hygiene articles, foods, food supplements, air fresheners, fragrances, pharmaceutical compositions and crop protection compositions.
3. The use according to embodiment 1 as formulation agent in preparations which comprise at least one scent substance and/or at least one aroma substance.
4. The use of compounds of the formula (I) for conveying, modifying and/or intensifying a musk scent note in a fragrance composition by admixing a sensually effective amount of at least one substance or of a substance mixture according to the definition in embodiment 1.
5. The use according to one of the preceding embodiments, where the compound of the formula (I) is used in stereoisomerically pure form or as E and Z mixture.
6. The use according to one of the preceding embodiments, where a stereoisomer mixture is used in which the weight fraction of 8-(E)-hexadeca-8,15-dienal, based on the total weight of (E)- and (Z)-hexadeca-8,15-dienal, is in a range from 1% to less than 100%, such as e.g. in a range from 5% to 95%, 15% to 85%, 25% to 75%, 40% to 60%, 45% to 55% or about 50%.
7. A process for the isolation of hexadeca-8,15-dienal, where an (E) and (Z) mixture of hexadeca-8,15-dienal is isolated from a reaction mixture, in particular from a by-product stream of the oxidation of cyclohexadeca-1,9-diene with nitrous oxide ($N_2O$) which comprises hexadeca-8,15-dienal.
8. The process according to embodiment 7, where hexadeca-8,15-dienal is isolated as (E) and (Z) mixture by means of fractional distillation.
9. The process according to embodiment 8, where hexadeca-8,15-dienal is isolated as (E) and (Z) mixture from a substance mixture which comprises a mixture of (E/Z)-hexadeca-8,15-dienal and cyclohexadec-8-enone, in which the weight fraction of (E/Z)-hexadeca-8,15-dienal, based on the total weight of (E/Z)-hexadeca-8,15-dienal and cyclohexadec-8-enone, is at least about 5%, such as e.g. about 10 to 65%.
10. The process according to embodiment 8 or 9, where hexadeca-8,15-dienal is isolated as (E) and (Z) mixture by means of a chromatographic method.
11. The process according to embodiment 10, where hexadeca-8,15-dienal is isolated as (E) and (Z) mixture from a substance mixture in which the weight fraction of (E/Z)-hexadeca-8,15-dienal, based on the total weight of the substance mixture, is at least about 35%, such as e.g. about 40 to 90%.
12. An aroma chemical composition, in particular fragrance or flavoring composition, comprising hexadeca-8,15-dienal according to the definition in one of embodiments 1 to 6.
13. The composition according to embodiment 12, comprising hexadeca-8,15-dienal according to the definition in one of embodiments 1 to 6 in a weight fraction of from 0.01 to 99.9% by weight, such as e.g. about 10 to 90, 15 to 85, 25 to 75, 40 to 60, 45 to 55% by weight, based on the total weight of the composition.
14. A composition comprising hexadeca-8,15-dienal according to the definition in one of embodiments 1 to 6.
15. The composition according to embodiment 14, comprising hexadeca-8,15-dienal according to the definition in one of embodiments 1 to 6 in a weight fraction of from 0.01 to 99.9% by weight, such as e.g. about 10 to 90, 15 to 85, 25 to 75, 40 to 60, 45 to 55% by weight, based on the total weight of the composition.
16. The composition according to embodiment 14 or 15, selected from perfumes, detergents and cleaners, cosmetic compositions, bodycare compositions, hygiene articles, foods, food supplements, air fresheners, fragrances, pharmaceutical compositions and crop protection compositions.
17. The use of hexadeca-8,15-dienal according to the definition in one of embodiments 1 to 6 for conveying, modifying and/or intensifying a musk scent note in a scent or aroma substance composition by admixing a sensorally effective amount of hexadeca-8,15-dienal.

c) Further Configurations of the Invention c1) Fragrance Compositions

According to a further aspect, the fragrances used according to the invention are used, especially for the purpose of more efficient handling and metering, also as fragrance mixtures with diluents or solvents. Here, the fraction of the fragrances, based on the sum of fragrances and solvents, is given in % by weight.

Solvent

In the context of the present invention, a "solvent" serves for the dilution of the fragrances to be used according to the invention or of the fragrance composition according to the invention without having its own odiferous properties. Some solvents have fixing properties at the same time.

The hexadeca-8,15-dienal can be admixed to a diluent or solvent in 1 to 99% by weight. Preference is given to at least 40% strength by weight solutions, further preferably at least 50% strength by weight solutions, furthermore preferably at least 60% strength by weight solutions, further preferably at least 70% strength by weight solutions, particularly preferably at least 80% strength by weight solutions, furthermore particularly preferably at least 90% strength by weight solutions, preferably in olfactorily acceptable solvents.

Preferred olfactory acceptable solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), benzyl benzoate (BB) and benzyl acetate. Here, preference is in turn given to ethanol, diethyl phthalate, propylene glycol, dipropylene glycol, triethyl citrate, benzyl benzoate and isopropyl myristate.

In the context of the present invention, a "fragrance composition" is a mixture which comprises at least one further fragrance alongside hexadeca-8,15-dienal. In particular, such a fragrance composition can be a perfume composition (a perfume oil).

Fragrance compositions according to the invention comprise, based on the total amount of the fragrance composition, e.g. an amount of hexadeca-8,15-dienal of from 0.01 to 65% by weight, preferably from about 0.1 to about 50% by weight, preferably from about 0.5 to about 30% by weight and particularly preferably from about 0.5 to about 25% by weight. The weight ratio of hexadeca-8,15-dienal to the total amount of further fragrances is e.g. in the range from 1:1000 to 1:0.5, preferably in the range from 1:700 to 1:1, particularly preferably in the range from 1:500 to 1:10.

Fragrance compositions according to the invention comprise, based on the total amount of the fragrance composition, e.g. an amount of hexadeca-8,15-dienal of from 0.01 to 65% by weight, preferably from about 0.1 to about 50% by weight, preferably from about 0.5 to about 30% by weight and particularly preferably from about 0.5 to about 25% by weight. The weight ratio of hexadeca-8,15-dienal to the total amount of further fragrances (different from hexadeca-8,15-dienal) is e.g. in the range from 1:1000 to 1:0.5, preferably in the range from 1:700 to 1:1, particularly preferably in the range from 1:500 to 1:10.

Further Fragrances

Besides hexadeca-8,15-dienal, fragrance compositions according to the invention comprise at least one further fragrance, preferably 2, 3, 4, 5, 6, 7, 8 or further fragrances, where further fragrances are selected e.g. from among:

Alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lilial[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methyi-cyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)propanal (Helional[3]), 3-(4-ethylpheny)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]). Within the context of the present invention, the aforementioned fragrances are accordingly preferably combined with mixtures according to the invention.

Where trade names are given above, these refer to the following sources:

[1] trade name of Symrise GmbH, Germany;
[2] trade name of Givaudan AG, Switzerland;
[3] trade name of International Flavors & Fragrances Inc., USA;
[5] trade name of Danisco Seillans S.A., France;
[9] trade name of Firmenich S.A., Switzerland;
[10] trade name of PFW Aroma Chemicals B.V., the Netherlands.

Further fragrances with which hexadeca-8,15-dienal can be combined e.g. to give a fragrance composition can be found e.g. in S. Arctander, Perfume and Flavor Chemicals, Vol. I and II, Montclair, N.J., 1969, self-published or K. Bauer, D. Garbe and H. Surburg, Common Fragrance and Flavor Materials, 4rd Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil;

cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil, thyme oil; tolubalsam; tonka absolute; tuberose absolute; vanilla extract; violet leaf absolute; verbena oil; vetiver oil; juniper berry oil; wine lees oil; wormwood oil; winter green oil; ylang ylang oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7tetramethyl 6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-

[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-(cis-2-penten-1-yl)-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzoyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-m ethylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnarnaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anehlole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

c2) Fragrance-Containing Articles

Hexadeca-8,15-dienal according to the invention or fragrance compositions according to the invention can be incorporated into a series of products or be applied to such products.

Fragrances according to the invention can be used in the production of perfumed articles. The olfactory properties, like the material properties (such as solubility in customary solvents and compatibility with further customary constituents of such products), as well as the toxicological acceptability of the fragrances according to the invention underline their particular suitability for the stated use purposes. The positive properties contribute to the fact that the fragrances used according to the invention and the fragrance compositions according to the invention are particularly preferably used in perfume products, body care products, hygiene articles, textile detergents, and in cleaners for solid surfaces.

The perfumed article is e.g. selected from perfume products, body care products, hygiene articles, textile detergents and cleaners for solid surfaces. Preferred perfumed articles according to the invention are also selected from among:

perfume products selected from perfume extracts, Eau de Parfums, Eau de Toilettes, Eau de Colognes, Eau de Solide, Extrait Partum, air fresheners in liquid form, gel-like form or a form applied to a solid carrier, aerosol sprays, scented cleaners and oils;

body care products selected from aftershaves, pre-shave products, splash colognes, solid and liquid soaps, shower gels, shampoos, shaving soaps, saving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, hair shampoo, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics such as e.g. eyeshadows, nail varnishes, make-ups, lipsticks, mascara, toothpaste, dental floss;

hygiene articles selected from candles, lamp oils, joss sticks, insecticides, repellents, propellants, rust removers, perfumed freshening wipes, armpit pads, baby diapers, sanitary towels, toilet paper, cosmetic wipes, pocket tissues, dishwasher deodorizer;

cleaners for solid surfaces selected from perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners;

textile detergents selected from liquid detergents, powder detergents, laundry pretreatments such as bleaches, soaking agents and stain removers, fabric softeners, washing soaps, washing tablets.

According to a further aspect, the fragrances used according to the invention and the fragrance compositions according to the invention are suitable for use in surfactant-containing perfumed articles. This is because fragrances and/or fragrance compositions with a musk note and pronounced naturalness are often sought—especially for the perfuming of surfactant-containing formulations such as, for example, cleaners (in particular dishwashing compositions and all-purpose cleaners).

According to a further aspect, fragrances used according to the invention and fragrance compositions according to the invention can be used as agents for providing (a) hair or (b) textile fibers with a rosy odor note.

The fragrances to be used according to the invention and fragrance compositions according to the invention are therefore particularly well suited for use in surfactant-containing perfumed articles.

It is preferred if the perfumed article is one of the following:

an acidic, alkaline or neutral cleaner which is selected in particular from the group consisting of all-purpose cleaners, floor cleaners, window cleaners, dishwashing detergents, bath and sanitary cleaners, scouring milk, solid and liquid toilet cleaners, powder and foam carpet cleaners, liquid detergents, powder detergents, laundry pretreatments such as bleaches, soaking agents and stain removers, fabric softeners, washing soaps, washing tablets, disinfectants, surface disinfectants, an air freshener in liquid form, gel-like form or a form applied to a solid carrier or as an aerosol spray, a wax or a polish, which is selected in particular from the group consisting of furniture polishes, floor waxes and shoe creams, or a body care composition, which is selected in particular from the group consisting of shower gels and shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics.

Ingredients with which fragrances used according to the invention or fragrance compositions according to the invention can preferably be combined are, for example: preservatives, abrasives, antiacne agents, agents to combat skin aging, antibacterial agents, anticellulite agents, antidandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emollients, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, detergents, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, aromas, flavorings, fragrances, polyols, surfactants, electrolytes, organic solvents or silicone derivatives.

According to a further aspect, the fragrances are used in the production of the perfumed articles in liquid form, undiluted or diluted with a solvent or in the form of a fragrance composition. Suitable solvents for this purpose are e.g. ethanol, isopropanol, diethylene glycol monoethyl ether, glycerol, propylene glycol, 1,2-butylene glycol, dipropylene glycol, diethyl phthalate, triethyl citrate, isopropyl myristate, etc. If the specified solvents have their own olfactory properties, they are assigned exclusively to the constituent "solvent" and not to the "fragrances".

The fragrances and/or fragrance compositions present in the perfumed articles according to the invention can in this connection, in one embodiment, be absorbed onto a carrier, which ensures both fine distribution of the fragrance or fragrance composition within the product and controlled release upon use. Carriers of this type may be porous inorganic materials such as light sulfate, silica gels, zeolites, gypsums, clays, clay granules, aerated concrete, etc. or organic materials such as woods and cellulose-based materials.

The fragrances used according to the invention and the fragrance compositions according to the invention can also be in microencapsulated form, spray-dried form, in the form of inclusion complexes or in the form of extrusion products and be added in this form to the product or article to be perfumed. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the perfume oil, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting fragrances used according to the invention and fragrance compositions according to the invention with a suitable wax-like substance and by extrusion with subsequent solidification, optionally in a suitable solvent, e.g. isopropanol.

c3) Isolation of Fragrances According to the Invention (E/Z)-Hexadeca-8,15-dienal is known e.g. from U.S. 2010 0191018.

Suitable sources for the isolation of (E/Z)-hexadeca-8,15-dienal is the by-product stream of the $N_2O$ oxidation of cyclohexadeca-1,9-diene, as described e.g. in U.S. 2010 0191018.

Reaction products of this type can then be worked up in a manner known per se in order to obtain the desired product in enriched form or in pure form.

Suitable methods are e.g. distillation processes, such as fractional distillation under atmospheric pressure or application of a vacuum; or column chromatography, such as SMB (simulated moving bed) chromatography or CAC (continuous annular chromatography).

The work-up can take place e.g. batchwise or continuously.

The invention will now be illustrated in more detail by reference to the following nonlimiting embodiments:

EXPERIMENTAL SECTION

Example 1: Isolation of (E/Z)-hexadeca-8,15-dienal by Fractional Distillation 2600 g of a mixture (crude product from oxidation of cyclohexadeca-1,9-diene with $N_2O$; as described e.g. in U.S. 2010 0191018) with about 6% (E/Z)-hexadeca-8,15-dienal were fractionally distilled in a batch column (fabric packing, 30 plates, top pressure: 5 mbar, pressure loss over column 5 mbar, bottom temperature: 180° C., Sambay evaporator, reflux ratio: 100). The mixture of (E/Z)-hexadeca-8,15-dienal was able to be enriched in the process in various fractions to 30, 37 and 65%.

Example 2: Synthesis of hexadeca-8,15-dienal by $N_2O$ oxidation of 1,9-cyclohexadecadiene In an adiabatic tubular reactor (3 m length, 6 cm diameter, 9 L reactor volume) filled with Raschig rings of 1.4541 stainless steel, 2000 g/h of 1,9-cyclohexadecadiene (cis/trans-isomeric mixture) were reacted with 52 mL/h of a $N_2O/CO_2$ mixture (15% $CO_2$ proportion) at 216° C. Molar ratio of olefin/$N_2O$/9-10. Unreacted 1,9-cyclohexadeca-1,9-diene was removed by distillation by means of a distillation column (Montz fabric packing A3, effective separation height 4000 mm, internal diameter 55 mm, feed at half height of the column) at a bottom temperature of 210° C. and a top pressure of 20 mbar. The bottoms discharge comprised ca. 5% by weight hexadeca-8,15-dienal (I) and less than 1% by weight of 1,9-cyclohexadecadiene.

Example 3: Isolation of (E/Z)-hexadeca-8,15-dienal by Column Chromatography 6 g of a mixture of (E/Z)-hexadeca-8,15-dienal (at least 35%) (from the fractional distillation of Example 1) were purified by means of column chromatography using a cyclohexane/MTBE eluent mixture (50:1). Following chromatographic purification, 1.8 g of the mixture (E/Z)-hexadeca-8,15-dienal were isolated with a purity of 90%. The isolated material was stored under an $N_2$ atmosphere.

$^1$H NMR (500 MHz, CDCl$_3$, 25° C.): ☐=9.8 (s, 1H), 5.85-5.75 (m, 1H), 5.4-5.3 (m, 2H), 4.9 (dd, 2H), 2.45-2.40 (m, 2H), 2.1-1.9 (m, 6H), 1.7-1.55 (m, 2H), 1.45-1.20 (m, 14H). $^{13}$C-NMR (125 MHz, CDCl$_3$, 25° C.): ☐=203 (2×CH$_2$), 139.2, 139.1, 130.5, 130.1, 130.0, 129.6, 114.2 (C═CH$_2$), 114.1 (C═CH$_2$), 43.9 (2×CH$_2$), 33.8 (2×CH$_2$), 32.5 (2×CH$_2$), 29.6, 29.5 (2×CH$_2$), 29.3, 29.1, 29.0 (2×CH$_2$), 28.8 (3×CH$_2$), 28.8, 28.6, 27.1 (2×CH$_2$), 22.0 (2×CH$_2$). IR (ATR) υ[cm$^{-1}$]=3082, 3000, 2935, 2864, 2809, 2710, 1742, 1638, 1455, 994, 968, 724. MS m/z=236, 165, 149, 121, 109, 95, 81, 67 (100), 55, 41.

Example 4: Olfactory Assessment

An (E)/(Z) substance mixture isolated by column chromatography (Example 2) was assessed hexadeca-8,15-dienal (E/Z) mixture),

| | |
|---|---|
| smelling strip test <1 min | green, soapy, musk character |
| smelling strip test 10 min | soapy, weakly floral, musk character |
| smelling strip test 30 min | soapy, weakly floral, musk character, aldehydic |
| smelling strip test 1 h | soapy, weakly floral, musk character, aldehydic |
| smelling strip test 24 h | musk-like |

The invention claimed is:

1. A method comprising adding hexadeca-8,15-dienal of the formula I

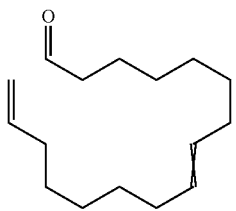

or a mixture which comprises this compound to a composition, wherein the hexadeca-8,15-dienal of the formula I acts as aroma chemical wherein the composition is selected from the group consisting of perfumes, detergents and cleaners, cosmetic compositions, bodycare compositions, hygiene articles, foods, food supplements, air fresheners, fragrances, pharmaceutical compositions and crop protection compositions.

2. The method according to claim 1 wherein the composition is a formulation which comprises at least one aroma chemical.

3. The method according to claim 1, wherein the composition is a fragrance composition, and the compound of the formula (I) is used for conveying, modifying and/or intensifying a musk scent note in the fragrance composition by admixing a sensorally effective amount of the hexadeca-8,15-dienal of the formula I or the mixture.

4. The method according to claim 1, where the compound of the formula (I) is used in stereoisomerically pure form or as 8-(E) and 8-(Z) mixture.

5. The method according to claim 1, where a stereoisomer mixture the hexadeca-8,15-dienal is used in which the weight fraction of 8-(E)-hexadeca-8,15-dienal, based on the total weight of (E) and (Z)-hexadeca-8,15-dienal, is in a range from 1% to less than 100%.

6. A composition comprising hexadeca-8,15-dienal of the formula I

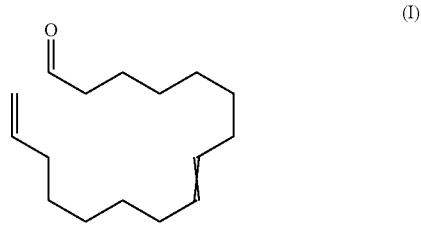 [SMILES: C=CCCCCCC=CCCCCCCC=O]

or of a substance mixture which comprises this compound as aroma chemical;

where the composition is selected from the group consisting of perfumes, detergents and cleaners, cosmetic compositions, bodycare compositions, hygiene articles, foods, food supplements, air fresheners, fragrances, pharmaceutical compositions and crop protection compositions.

7. The composition according to claim 6, comprising the hexadeca-8,15-dienal of formula I in a weight fraction of from 0.01 to 99.9% by weight, based on the total weight of the composition.

8. The method according to claim 1, where a stereoisomer mixture the hexadeca-8,15-dienal is used in which the weight fraction of 8-(E)-hexadeca-8,15-dienal, based on the total weight of (E) and (Z)-hexadeca-8,15-dienal, is in a range from 25% to 75%.

* * * * *